(12) United States Patent
Rapp

(10) Patent No.: US 12,186,158 B2
(45) Date of Patent: Jan. 7, 2025

(54) NEGATIVE PRESSURE THERAPY SYSTEMS AND SPONGES

(71) Applicant: Fiomet Ventures, Inc., Cincinnati, OH (US)

(72) Inventor: Scott Rapp, Cincinnati, OH (US)

(73) Assignee: FIOMET VENTURES, INC., Cincinnati, OH (US)

( * ) Notice: Subject to any disclaimer, the term of this patent is extended or adjusted under 35 U.S.C. 154(b) by 0 days.

(21) Appl. No.: 18/388,200

(22) Filed: Nov. 9, 2023

(65) Prior Publication Data

US 2024/0074909 A1 Mar. 7, 2024

Related U.S. Application Data

(63) Continuation of application No. 17/165,992, filed on Feb. 3, 2021, now Pat. No. 11,850,121, which is a continuation of application No. 15/482,877, filed on Apr. 10, 2017, now Pat. No. 10,959,884.

(60) Provisional application No. 62/319,852, filed on Apr. 8, 2016.

(51) Int. Cl.
| | |
|---|---|
| *A61F 13/00* | (2024.01) |
| *A61F 13/01* | (2024.01) |
| *A61F 13/05* | (2024.01) |
| *A61F 13/0203* | (2024.01) |
| *A61F 13/0206* | (2024.01) |

(52) U.S. Cl.
CPC .. *A61F 13/01008* (2024.01); *A61F 13/00055* (2013.01); *A61F 13/05* (2024.01); *A61F 2013/00174* (2013.01); *A61F 2013/00536* (2013.01); *A61F 13/01029* (2024.01); *A61F 13/01034* (2024.01); *A61F 13/0206* (2013.01); *A61F 13/022* (2013.01)

(58) Field of Classification Search
CPC ............ A61F 13/00068; A61F 13/0216; A61F 2013/00536; A61F 2013/00174; A61F 13/00029; A61F 13/022; A61F 13/0206; A61F 13/00008; A61F 13/00034
See application file for complete search history.

(56) References Cited

U.S. PATENT DOCUMENTS

| | | | |
|---|---|---|---|
| 6,695,823 B1 | 2/2004 | Lina et al. | |
| 9,421,132 B2 | 8/2016 | Dunn | |
| 2003/0108587 A1 | 6/2003 | Orgill et al. | |
| 2011/0060204 A1* | 3/2011 | Weston | A61M 1/962 604/319 |
| 2011/0315204 A1 | 12/2011 | Gleason et al. | |
| 2013/0116641 A1 | 5/2013 | Hicks | |
| 2014/0180225 A1 | 6/2014 | Dunn | |
| 2015/0231314 A1 | 8/2015 | Robinson et al. | |

* cited by examiner

*Primary Examiner* — Kai H Weng
(74) *Attorney, Agent, or Firm* — BUSINESS PATENT LAW, PLLC

(57) ABSTRACT

Negative pressure wound therapy sponges that are custom-fabricated to fit a given wound to be treated, corresponding methods of creating said sponges in situ or external to a wound, and related systems for performing negative pressure wound therapy using said sponges. Exemplary sponge embodiments may have pressure-sensing capabilities.

14 Claims, 12 Drawing Sheets

*Surface and 3-D Pressure Mapping*

Red = Negative Pressure
Green = Positive Pressure
Yellow = Zero Pressure

NEGATIVE PRESSURE THERAPY SYSTEMS AND SPONGES

RELATED APPLICATIONS

This application claims priority to U.S. application Ser. No. 17/165,992—Negative Pressure Therapy Systems and Sponges—, filed Feb. 3, 2021 that claims priority to U.S. application Ser. No. 15/482,877—Pressure-Sensing Negative Pressure Therapy Sponges and Methods for the Creation and use thereof—, filed Apr. 10, 2017, now U.S. Pat. No. 10,959,884, issued Mar. 30, 2021, that claimed the benefit of U.S. Provisional Application 62/319,852, filed Apr. 8, 2016.

TECHNICAL FIELD

Exemplary system and method embodiments described herein are directed to customized sponges and the use thereof in negative pressure therapy and similar wound treatment procedures.

BACKGROUND

Wound care is currently a seven-billion-dollar annual market worldwide. With a rapid rise in cases, the U.S. alone is said to spend 1-2 billion dollars on wound care annually. (See, e.g., Bergstrom N, Allman R M, Carlson C E, Eaglstein W, Frantz R A, Garber S L, et al., Pressure ulcers in adults: prediction and prevention. Rockville (Md.): US Department of Health and Human Services, Public Health Service, Agency for Health Care Policy and Research; 1992, p. 1, which is hereby incorporated by reference.) This escalation of costs adds to the ongoing global medical financial burden. Such strain on the medical system even led the Centers for Medicare & Medicaid Services in 2011 to stop reimbursements for certain wounds felt to be iatrogenic. Consequently, much efforts have been dedicated to wound care research and interventions that may lead to rapid recovery and healing.

The cause behind the rise in the incidence of wounds requiring extended therapy is multifactorial. For example, an acute or chronic wound can result from trauma, infection, malnutrition, vascular insufficiency, prolonged immobility and decreased tissue perfusion pressure, or any combination of the above. Obesity is frequently a contributing factor, and is currently an endemic problem facing an estimated 35%, or 80 million, people in the U.S. alone, with an estimated medical burden of 147 billion dollars. Morbidities associated with obesity include Type II Diabetes Mellitus (20 million sufferers) and peripheral vascular disease (8 million sufferers). Worldwide, it is estimated that diabetes affects 347 million people.

Common to both diabetes and peripheral vascular disease is the prevalence of chronic skin wounds. Diabetes affects the microvascular patency and results in neuropathies and skin perfusion compromise. Diabetics often suffer from lower extremity wounds due to the decreased sensation preventing trauma and resulting inability to deliver adequate blood supply to the region to heal the wounds. Hyperglycemia also affects wound healing dynamics. Exacerbated by smoking, hypertension, elevated cholesterol, etc., peripheral vascular disease also contributes to a large number of chronic wounds. Ischemia to end organs (i.e., skin) leads to ulceration and tissue breakdown. Again, poor perfusion to the wounds prevents healing capacity.

Chronic wounds are present in an estimated 6.5 million people in the U.S. The associated direct and indirect costs to the healthcare system is an estimated 25 billion dollars annually. (See, e.g., Sen C K, Gordillo G M, Roy S, et al. Human skin wounds: a major and snowballing threat to public health and the economy; Wound Repair Regen. 2009; 17(6):763-771, which is hereby incorporated by reference.) A subset of peripheral vascular disease includes what is known as chronic venous insufficiency (CVI), which is generally defined as a skin wound that is present usually below the knee for a period of greater than four weeks. It is estimated that these wounds affect 1-4.3% of the Western population, with a greater prevalence in the adult population over the age of 65. The average time to healing of a CVI is approximately 12 months, and approximately 28% of sufferers will experience more than ten episodes of ulceration in their lifetimes. (See, e.g., Graham I D, Harrison M B, Nelson E A, Lorimer K, Fisher A. Prevalence of lower-limb ulceration: a systematic review of prevalence studies; Advances in Skin and Wound Care 2003; 16:305-16, which is hereby incorporated by reference.) (See, e.g., Margolis D J, Bilker W, Santanna J, Baumgarten M (2002) Venous leg ulcer: incidence and prevalence in the elderly. J Am Acad Dermatol 46: 381-386, which is hereby incorporated by reference.) In this regard, the overall 5-year recurrence rate is up to 78%. (See, e.g., Cost-Effective Use of Silver Dressings for the Treatment of Hard-to-Heal Chronic Venous Leg Ulcers. Jemec G B, Kerihuel J C, Ousey K, Lauemoller S L, Leaper D J. PLoS One. 2014 Jun. 19; 9(6):e100582. doi: 10.1371/journal.pone.0100582. eCollection 2014, which is hereby incorporated by reference.) Notably, there is also a 2.5% mortality rate associated with any chronic wound. (See, e.g., Argenta L C, Morykwas M J, Marks M W, DeFranzo A J, Molnar J A, David L R. Vacuum-assisted closure: State of clinic art. Plast Reconstr Surg. 2006; 117(Suppl):127S-142S, which hereby incorporated by reference.)

The psychological effects from chronic wounds are major inhibitors to a person's quality of life and intrusion to activities of daily living. Negative impacts include psychological stresses that involve depression, anxiety, fear, and emotional disorders 10. Patients develop a perceived societal marginalization leading to the stigma, social withdrawal and isolation. A lack of intimate relationships, decrease in overall mood and lack of social support contributes to diminished work productivity. There may be difficulties with acquiring healthcare coverage to compound days at work lost. The total economic financial cost of the above is largely incalculable.

Wounds resulting from prolonged immobility in the operating theater are also frequent. General anesthesia often involves paralysis of the muscles to assist with surgery, and without muscular contraction, it is difficult for the body to prevent ischemia to tissues over areas of bony prominences. Tissue ischemia occurs when perfusion pressures fall below the externally applied pressures. Areas such as the ischium, trochanteric area, elbows, knees, scalp, and heels are particularly prone to ulceration due to ischemia.

It is generally accepted that tissue ischemia may occur when externally applied pressures are greater than 32 mmHg for over 2 hours on a particular body area. Thus, skin breakdown from ischemia may also result in as little as two hours when a patient is paralyzed by general anesthesia (or otherwise). Preventive techniques associated with ischemia (i.e., with alleviating/preventing the application of excessive externally applied pressures) commonly involve the placement of foam padding, gels and bumps. The particular problem in the operating theater is that trained physicians/ancillary staff often make incorrect subjective assumptions after visual inspection that perfusion pressures to the skin tissue are adequate. Furthermore, longer surgeries tend to lead to a greater likelihood of ulcer formation. For example, it has been suggested that when a surgery lasts for more than four hours, each additional thirty minutes thereafter leads to a 33% increase in ulcer formation. (See, e.g., Schoonhoven L, Defloor T, Grypdonck M H. Incidence of pressure ulcers due to surgery. J Clin Nurs. 2002; 11(4):479-487, which is hereby incorporated by reference.) Neurosurgery cases, in particular, have an estimated 44% incidence of up to grade II ulcers. (See, e.g., Furuno Y, Sasajima H, Goto Y, Taniyama I, Aita K, Owada K, Tatsuzawa K, Mineura K. Strategies to prevent positioning-related complications associated with the lateral suboccipital approach. J Neurol Surg B Skull Base. 2014 February; 75(1):35-40, which is hereby incorporated by reference.)

Unfortunately, operating room-acquired ulcers are said to cost the U.S. health care system between 750 million and 1 billion dollars annually. (See, e.g., Beckrich K, Aronovitch S A. Hospital-acquired pressure ulcers: A comparison of costs in medical vs. surgical patients. Nurs Econ. 1999; 17:263-2712, which is hereby incorporated by reference.) And, the estimated annual cost associated with a hospital acquired ulcer is estimated to be $43,180 on an individual patient basis. (See, e.g., Armstrong D. G., Ayello E. A., Capitulo K. L., Fowler E., Krasner D. L., Levine J. M., Sibbald R. G., Smith A. P. S. (2008). New opportunities to improve pressure ulcer prevention and treatment: Implications of the CMS inpatient hospital care present on admission (POA) indicators/hospital-acquired conditions (HAC) policy. A consensus paper from the International Expert Would Care Advisory Panel. Journal of Wound, Ostomy and Continence Nursing, 35 (5), 485-492, which is hereby incorporated by reference.) Chronic wounds are often clinically described by an ulcer classification grade. Grade I ulcers are wounds where the skin is intact, but erythematous and red. Usually pressure relief rectifies this ulcer. Grade II ulcers have skin breakdown and dermis exposed. Local wound care is usually all that is needed to treat and prevent infection of such an ulcer. This is usually through dressings and topical antibiotics in a moist atmosphere. An example of a grade II ulcer is blistering and a chronic draining wound. Grade III ulcers are full thickness defects through the skin, and may expose the underlying fascia. Grade IV ulcers occur when there is a wound with a depth through the muscle that is sufficient to expose underlying bone.

Negative pressure wound therapy (NPWT) or vacuum assisted closure (VAC) to treat grade II-IV ulcers and most significant wounds has become the gold standard and has been described in medical literature since 1997. (See, e.g., Morykwas M J, Argenta L C, Shelton-Brown E I, et al. Vacuum-assisted closure: a new method for wound control and treatment: animal studies and basic foundation. Ann Plast Surg. 1997; 38:553-562, which is hereby incorporated by reference.) Negative pressure therapy has been demonstrated to decrease wound healing times, improve granulation formation, and help manage fluid output. Kinetic Concepts Inc. (KCI), in San Antonio, Tex. currently dominates the NPWT market, with a reported 1.6 billion dollars in annual global revenue (as of 2011). (See, e.g., Data acquired from website: http://www.kci1.com/KCI1/corporateprofile on Jan. 7, 2016, which is hereby incorporated by reference.) The types of the 8 billion wounds KCI claims their NPWT unit was applied to include: open abdomen management, incision management, chronic wounds, acute wounds, traumatic wounds, sub-acute wounds, dehisced wounds, partial thickness burns, diabetic ulcers, pressure ulcers, flaps and grafts, venous stasis ulcers, arterial ulcers, and venous leg ulcers.

The KCI device works theoretically by many mechanisms. (See, e.g., Orgill D P, Bayer L R. Negative pressure wound therapy: past, present and future. Int Wound J. 2013 December; 10 Suppl 1:15-9, which is hereby incorporated by reference.) For example, the device is thought to create macrodeformation whereby the device mechanically brings wound edges together through a collapsible sponge placed in the wound. When negative pressure is applied to the closed system, the sponge collapses and therefore contracts the wound. There is both positive and negative pressure within this sponge. It is thought that angiogenesis and improved granulation tissue formation may be a result of the positive pressure created where the wound edges are faced. Furthermore, mechanical stretch of tissue or microdeformation, lower oxygen gradients, and the creation of a mild ischemic atmosphere may promote systemic growth factor release to the wound and thus accelerate healing. There may also be a decrease in the inflammatory process in the wound associated with mast cell presence. The negative pressure in the central portion of the sponge additionally assists with fluid removal and thus helps to facilitate wound healing. It is also claimed that negative pressure therapy increases blood flow to the wound, thereby also improving healing times.

Despite the widespread use and accepted value of NPWT, the specifics of how to optimally use negative pressure therapy or vacuum assisted closure therapy have yet to be objectively determined. Currently, suggested acceptable negative pressures range from between −75 mmHg to −125 mmHg, in a continuous or intermittent phase of pressure application. The most common devices use an electrically-powered portable pneumatic pump. Negative pressures are achieved through vacuum-type suction, with pressure readings taken either at the wound dressing interface or at the pump motor itself. The accepted therapeutic negative pressures to be applied during negative pressure therapy have thus far been based on limited animal model data. (See, e.g., Morykwas M J, Argenta L C, Shelton-Brown E I, McGuirt W. Vacuum-assisted closure: a new method for wound control and treatment: animal studies and basic foundation. Ann Plast Surg. 1997 June; 38(6):553-62, which is hereby incorporated by reference). This data may not correlate well with human tissue healing, as very few animal models have similar anatomic and physiologic features as human skin. Furthermore, wounds are different in size, depth, contamination and clinical severity. Using the same pressure for every wound is not ideal. Consequently, the optimal negative pressure by which to promote wound healing is largely anecdotal and, frankly, commonly just a guess made by a clinician. Typically, a negative pressure dressing is changed every 3-5 days to minimize the risk of infection. The associated sponge also needs to be changed frequently, as it becomes clogged with fibrinous tissue, granulation tissue, necrotic debris, and bacteria, which tends to prevent fluid removal. The application is not sterile and the wound can quickly become colonized with bacteria, which can ultimately prevent a maximal wound healing environment.

Patients complain that currently available NPWT pumps are bulky, loud, and costly. Alarms constantly go off regarding leaks in the system, inadequate pressures or pump failure. The vacuum pump and collecting canister is bulky and prevents mobility. The noise level of the active pump interrupts patient's sleep. A negative pressure of −125 mmHg, or the most common negative pressure used clinically, may cause discomfort to the patient and may be excessively high for optimized healing of the particular wound to which NPWT is being applied.

An important modification to the known KCI system was the implementation of a track device, which allows modification of the negative pressures by the pump as the patient ambulates. Alarms commonly now also produce an alert when a leak is detected or when excessive pressure or fluid output is occurring, so as to prevent major problems. The limitations on portability, size, and noise levels have led to alternative products on the market. For example, spring-assisted negative pressure, more manageable canister sizes, smaller pumps, and lower cost materials, have been developed. (See, e.g., Scalise A, Calamita R, Tartaglione C, Pierangeli M, Bolletta E, Gioacchini M, Gesuita R, Di Benedetto G. Improving wound healing and preventing surgical site complications of closed surgical incisions: a possible role of Incisional Negative Pressure Wound Therapy. A systematic review of the literature. Int Wound J. 2015 Oct. 1, which is hereby incorporated by reference.)

Alterations to the sponges used in NPWT have also been tested. However, the balance of sponge compression to the ability of a sponge to promote mechanical creep of surrounding tissue while still allowing for fluid removal, has proven difficult to optimize. The NPWT sponges currently on the market have been refined and made more uniform. There are now two types of sponge foam available—a polyurethane "black" foam with pore sizes of between 400-600 μm, and a polyvinyl alcohol "white" foam of higher density that better prevents the accumulation of large amounts of granulation tissue. Existing NPWT sponges may also be coated with silver to prevent increased microbial loads.

Despite long term use of NPWT and improvements to the components thereof, complications to conventional NPWT therapy are many. Since issuing the Nov. 13, 2009 Preliminary Public Health Notification and Advice for Patients (which is hereby incorporated by reference), the FDA has received reports of an additional six deaths and 97 injuries related to NPWT, for a total of 12 deaths and 174 injury reports since 2007. (See, e.g., Data acquired from website: http://www.fda.gov/Medi calDevices/Safety/AlertsandNotices/ucm244211.htm on Jan. 7, 2016, which is hereby incorporated by reference.) More than half of these incidences are related to sponge fragments being retained in a wound and subsequent resulting infection. There have been reports of toxic shock syndrome due to retained sponges. Major bleeding has been reported and said to be responsible for deaths when the wound VAC is placed near a major arterial repair (vascular surgery). Deaths can also be attributed to using wall suction and unregulated negative pressure—a direct result from our lack of optimization of individual pressures for each individual wound.

From the foregoing description, it should be apparent that there is an unmet need for improved components and methodologies in the arena of negative pressure wound therapy. Exemplary negative pressure therapy sponge embodiments and the associated methods of use described herein satisfy this need.

SUMMARY

Exemplary negative pressure therapy sponge embodiments according to this application represent an improvement in multiple aspects over existing negative pressure wound therapy or wound VAC technology. The exemplary embodiments described herein embody advances in the design of the adhesive tape used in negative pressure therapy treatments, the sponge that is placed in the wound, the sensing capability of the negative pressure therapy system, and the user interface provided to assist a user in optimizing wound treatment parameters.

To address the fact that no wound is exactly alike with respect to size, depth, and clinical appearance, exemplary embodiments described herein include a custom-fabricated negative pressure therapy sponge. The creation and use of a custom-fabricated sponge will allow the sponge fill exactly the wound that the associated negative pressure therapy is attempting to treat. Further, instead of using multiple conventional foam sponges to fill deep, irregular or large holes, as is currently required, exemplary sponge embodiments will be able to evenly fill every portion and gap of a wound—even a deep, irregular or large wound (see e.g., FIG. 1). The use of exemplary sponge embodiments will also, among other things, facilitate prevention of foreign body retention in the wound, which may lead to infection or death.

Other aspects and features of the invention will become apparent to those skilled in the art upon review of the following detailed description of exemplary embodiments along with the accompanying drawing figures.

BRIEF DESCRIPTION OF THE DRAWINGS

In the following descriptions of the drawings and exemplary embodiments, like reference numerals across the several views refer to identical or equivalent features, and.

DETAILED DESCRIPTION OF THE EXEMPLARY EMBODIMENTS

As described above, exemplary negative pressure therapy sponge embodiments are custom-fabricated to correspond to size, shape and contours of a given wound, and to evenly fill the wound. At least some exemplary negative pressure therapy sponge embodiments may be created by injecting foam components into a wound and allowing the foam components to react, expand, and fill the wound. Other exemplary negative pressure therapy sponge embodiments may be produced by creating a digital 3-D model of a wound (such as by imaging with a camera, laser or the like) and then 3-D printing a custom negative pressure therapy sponge.

Exemplary negative pressure therapy sponge embodiments may be comprised of materials such as, for example, open cell silicones. Such materials may have a density of between, for example, 0.18 and 0.25 g/cm 3. Without limitation, one exemplary silicone-based material that may be used polydimethylsiloxane (PDMS) silicon rubber. Silicone-based products are well-suited as a custom negative pressure therapy sponge material due to their biocompatibility, and reduced skin irritation and cytotoxicity.

Figure 1:
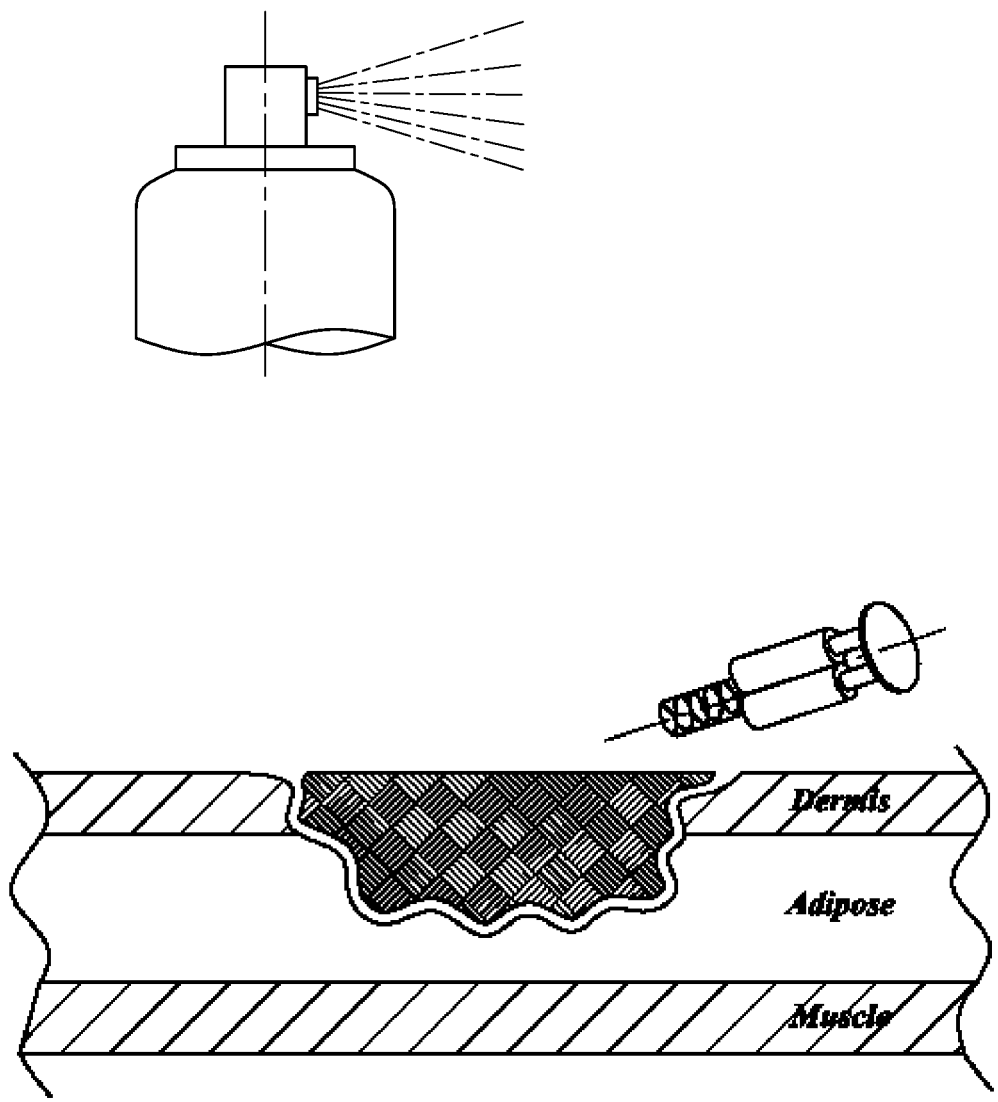
FIG. 1 depicts the creation and placement of one exemplary negative pressure therapy sponge embodiment within an open wound of a patient.

An alternative composition for producing an exemplary negative pressure therapy sponge embodiment may be polyurethane, polyester, polyether or a variant/combination. For example, an exemplary negative pressure therapy sponge embodiment may be comprised of a mixture of polymeric diphenylmethane diisocyanate (Iso, MDI), polyol (polyether glycerol, polyether glycol), and catalyst (33% triethylenediamine (TEDA), 66% dipropylene glycol (DPG)). The materials may be reticulated and may possess viseoelastic properties. One non-limiting example of suitable soft foam may be created with a relative density of about 5.2 lb/cubic ft. Such a mixture may comprise, for example and without limitation, 1.5 g catalyst and 43 g iso per 100 g polyol. Increasing concentrations of iso to polyol result in foams of increasing density and firmness. As represented in FIG. 1, in one exemplary embodiment, the selected sponge material (e.g., silicone) is initially provided in multi-component liquid form, which liquid components are injected via a syringe-type applicator into a wound of interest and allowed to react to create a custom negative pressure therapy sponge with open cell pores that conforms to the exact shape and contours of the wound.

FIG. 1 also represents an alternative technique for creating an exemplary negative pressure therapy sponge. As illustrated in the upper left corner of FIG. 1, an aerosolized foam material may be employed instead of a foam dispensed from a syringe-type applicator. In this case, the aerosolized foam would be sprayed into a wound of interest and allowed to react to create a custom negative pressure therapy sponge with open cell pores that conforms to the exact shape and contours of the wound.

Figure 2:
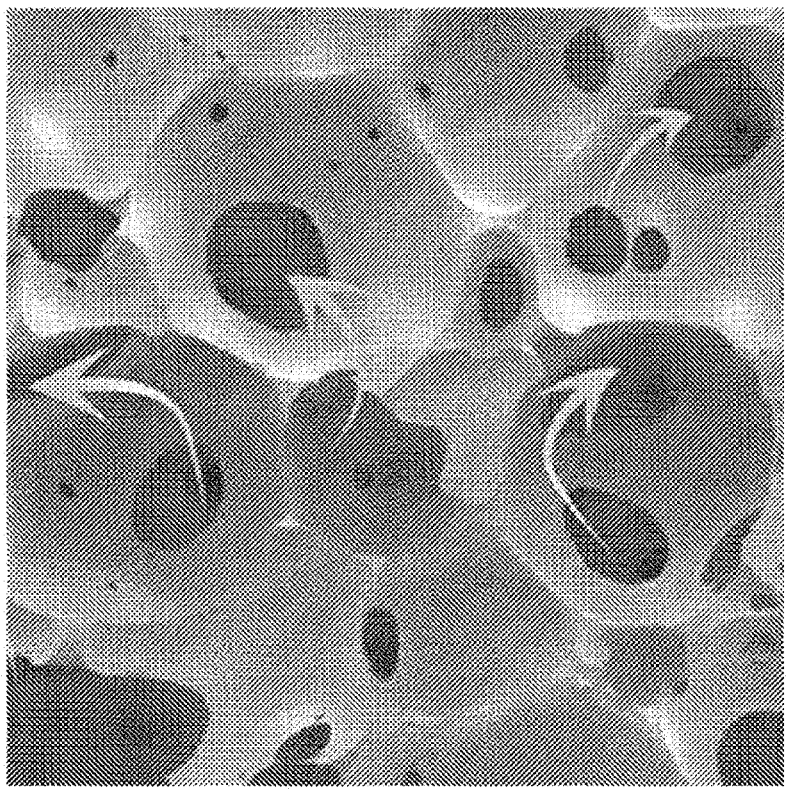
FIG. 2 is a magnified view of one exemplary foam material from which an exemplary negative pressure therapy sponge embodiment may be manufactured.

As illustrated in FIG. 2, the foam sponge resulting from either creation technique shown in FIG. 1 is preferably an open-cell solid structure with pore sizes ranging from, for example, 200-1,000 µm (FIG. 2). The pore size may be determined by the plastic bubble or cell formation with mechanical oscillation of the materials to arrive at the desired pores per inch (ppi).

Figure 3:
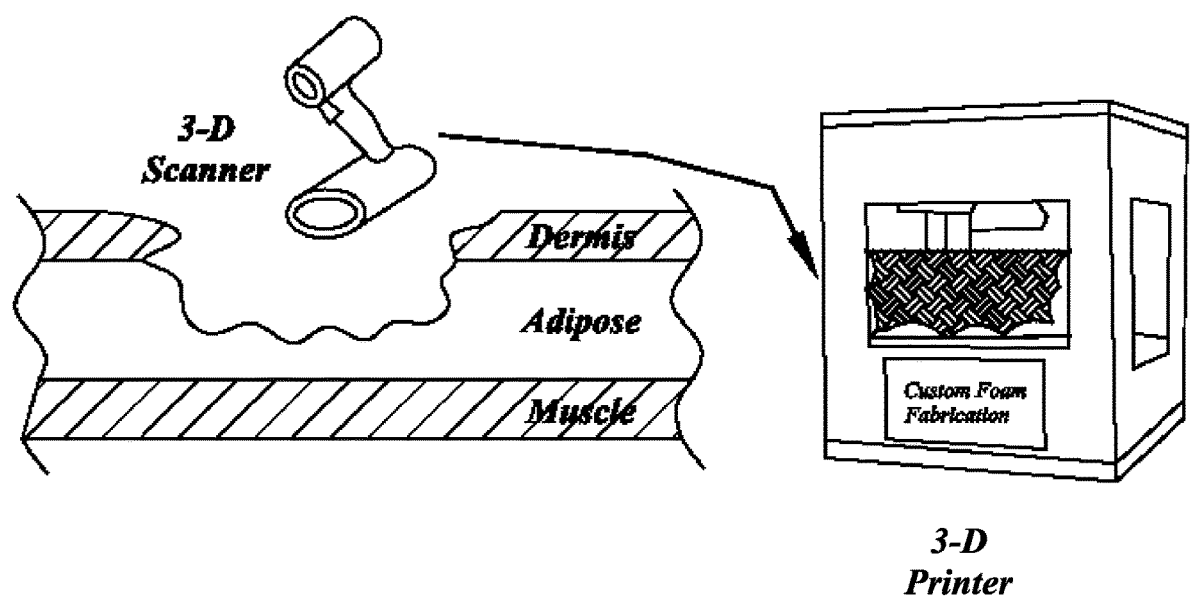
FIG. 3 illustrates other techniques for creating an exemplary negative pressure therapy sponge embodiment.

As represented in FIG. 3, an exemplary negative pressure therapy sponge embodiment may also be created using a 3-D printer. More specifically, a wound of interest would first be imaged, such as through conventional 3-D reconstructions, a CT scan, 3-D photography, laser scanning, etc. In FIG. 3, a portable 3-D scanner (camera) is used to capture wound images from a patient's bedside. In any case, the imaging process is used to create a digital 3-D wound model that may be sent to a device such as, but not limited to, a 3-D printer. The 3-D printer or other sponge forming device is then used to create a custom negative pressure therapy sponge from the digital 3-D wound model, such that the sponge will precisely fit within and evenly fill the wound. When a device such as a 3-D printer is used to create an exemplary negative pressure therapy sponge embodiment, the desired pore size may be set with viseoelastic properties customized to the wound being treated. For example, a deep narrow wound may have more rigid compression properties and larger pore sizes to prevent debris and fluid from disrupting fluid removal capability.

It should be realized that the above-described and shown exemplary techniques for producing an exemplary custom negative pressure therapy sponge allow for the creation of a custom sponge at each dressing change (if warranted). Consequently, as the size, shape and interior contours of a given wound change during the healing process, exemplary negative pressure therapy sponges may be easily custom-fabricated to accommodate such changes, thereby ensuring that the sponge used will always properly fit the wound during all stages of healing.

Figure 4:
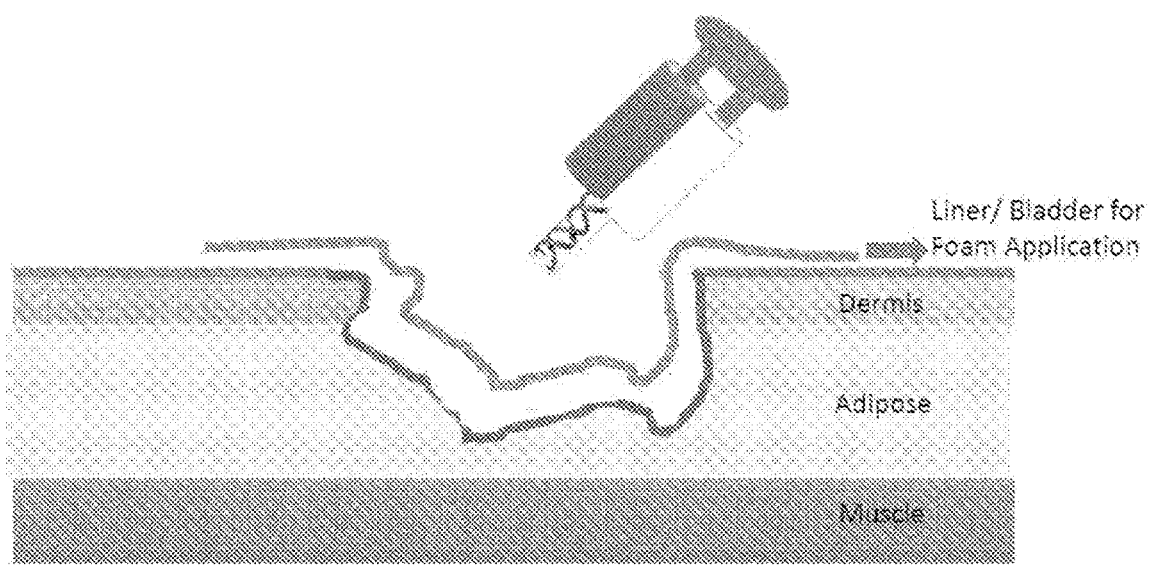
FIG. 4 depicts the creation and placement of one exemplary negative pressure therapy sponge embodiment within an open wound of a patient using liner/bladder within the wound to receive the sponge material.

As illustrated in FIG. 4, a bladder or liner may be placed into a wound prior to foam application to permit the foam to harden prior to tissue contact while still achieving the desired wound-conforming, custom shape. The bladder/liner materials may be, for example, plastic, silicone, polyurethane, etc. For example, the bladder/liner may be a thin polyurethane, Mylar®, silicone-based, or other plastic based sheet material. The bladder/liner may be similar in thickness to a Tegaderm™ tape (available from 3M Healthcare in St. Paul, Minn.). After the foam hardens, the resulting custom negative pressure therapy sponge and the bladder/liner may be removed, the custom negative pressure therapy sponge may then be re-inserted into the wound. The foam chemicals may be aerated while being mixed within the bladder/liner to allow for proper creation of pores.

The foam used to form a given exemplary negative pressure therapy sponge embodiment may be compressible at −125 mmHg of negative pressure, but not compressible at −50 mmHg of negative pressure. The pore size employed may be selected based on the amount of microdeformation desired. More microdeformation will be produced when the pore size is between about 500-1,000 µm. Prevention of pore size closure will allow for fluid exudate removal.

When no pressure is applied to an exemplary negative pressure therapy sponge located within a wound, the foam of the sponge will remain in its resting state. An applied negative pressure using an appropriate NPWT device will cause the sponge material to collapse, but it will return to its resting state upon removal of the negative pressure. An exemplary negative pressure therapy sponge embodiment may be removed from a wound without pieces of the sponge breaking off and remaining as foreign bodies within the wound.

The pore size of an exemplary negative pressure therapy sponge embodiment may be predetermined to maximize the promotion of granulation tissue formation, cellular proliferation, and vascular in-growth. The pore size of an exemplary negative pressure therapy sponge embodiment may also be designed to mildly adhere to the wound bed such that debridement occurs at each sponge removal. An exemplary negative pressure therapy sponge embodiment may also be coated with antimicrobial materials such as, for example, silver, chlorhexidine, iodine, or other antimicrobial agents. To provide rigidity to the negative pressure therapy sponge structure, exemplary embodiments may be nano coated with materials such as, for example, carbon, anodized carbon, silicon dioxide, silicone, silica, fiberglass, PTFE or equivalent fortifying materials. Coating the open cell foam will generally not reduce the pore size.

In certain embodiments, the pressure sensing sponge is coated with wound modifying substances. For example, the sponge may be coated or bioprinted with growth factors or stem cells. Growth factor families such as Vascular Endothelial Growth Factor (VEGF), Insulin-like Growth Factor (IGF), Fibroblast Growth Factor (FGF), Platlet-derived Growth Factor (PDGF), Bone Morphogenetic Protein (BMP), Epidermal Growth Factor (EGF), transforming growth factor (TGF), Keratinocyte Growth Factor (KGF), Colony Stimulating Factors, Tropoelastin, Interleukins, Collagens or the like may be added both to the sponge or 2-part silicone preparation to improve wound healing capacity.

Also in accordance with alternative embodiments, Autogenous or Allograft stem cells such as embryonic stem cells, tissue specific stems cells including Mesenchymal Stem Cells (MSCs), Adipose-derived Stem Cells (ASCs), Pericyte-derived stem cells (PSCs), hematopoietic stem cells, or epithelial stem cells can be bioimprinted on to the sponge materials. Alternatively, chemical wound debriding substances can be added to the sponge materials to assist with necrotic tissue removal, harmful metalloproteinase breakdown and accelerate healing. Enzymatic debriding products can be added to the final sponge or 2-part system including collagenase based products, papain based products, papain-urea based products, hydrogels, or other equivalent autolytic debriders. Other possible autolytic agents include: elastase, myeloperoxidase, acid hydrolase, and lysosomal enzymes.

Figure 5:
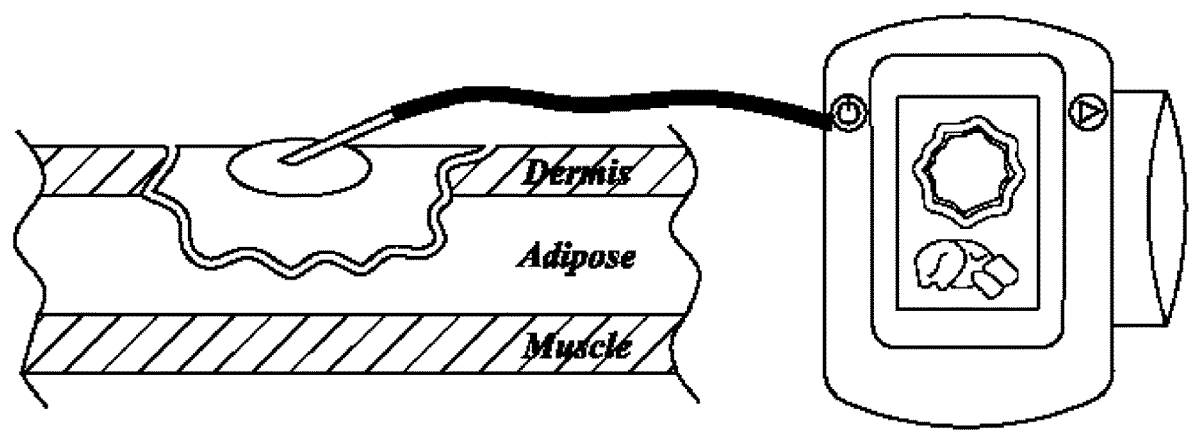
FIG. 5 represents a sensor placed on the surface of an exemplary negative pressure therapy sponge embodiment that is located in the wound of a patient, along with an associated exemplary monitor/controller for presenting sensor data to a user.

As represented in FIG. 5, the use of exemplary negative pressure therapy sponge embodiments may include wound monitoring. That is, whether a negative pressure therapy sponge embodiment is created in-situ as described above, prefabricated using, for example, a 3-D printing process, or even non-custom, the foam used to create the sponge will be pressure sensing in nature. To that end, an exemplary negative pressure therapy sponge embodiment may be coated with silver, zinc oxide, anodized carbon, copper, Au NPs, other carrier vehicles, other piezoelectric materials or pressure-sensing nanotechnology. When coated, such an exemplary sponge may be coated only along the circumference or on all material surfaces. In any case, the applied electroactive coating will have high electrical conductivity and be resistant to oxidation. The coating will also adhere well to the underlying sponge material.

Figure 7:
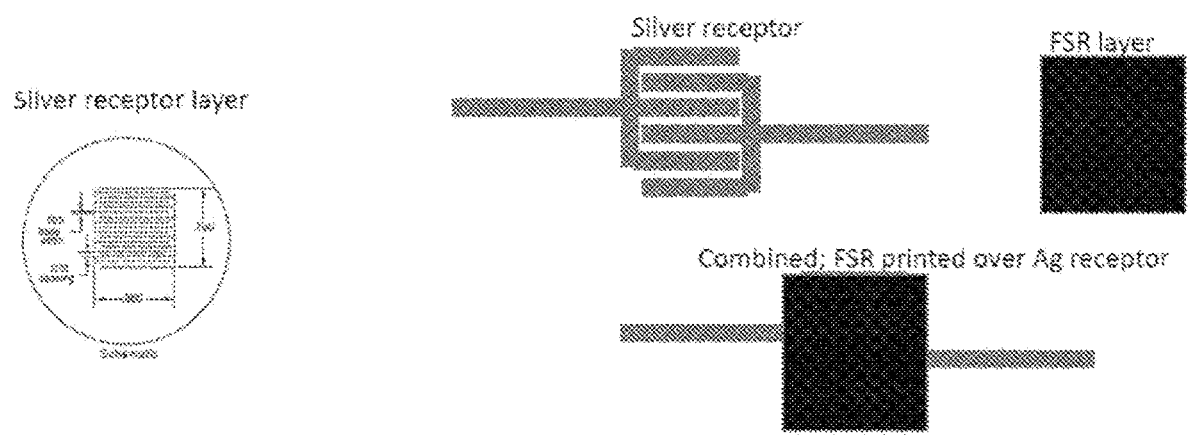
FIG. 7 depicts one exemplary embodiment of a force-sensing resistor (FSR) that may be utilized as a sensor for placement on the surface of an exemplary negative pressure therapy sponge embodiment.

FIG. 7 represents one type of pressure sensor that may be employed in a pressure-sensing exemplary negative pressure therapy sponge embodiment. In this particular example, the force sensor is a force-sensing resistor. However, other sensor types may be used in other embodiments.

Figure 6:
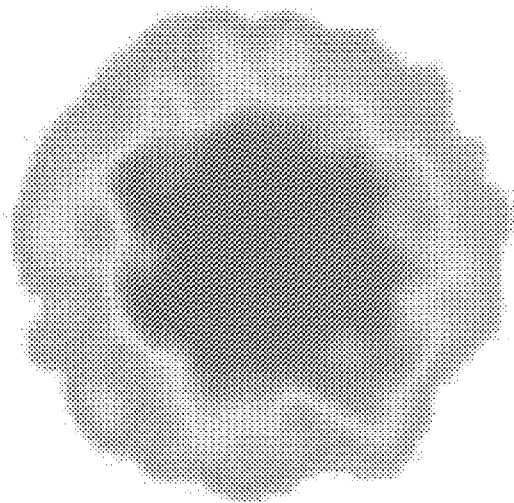
FIG. 6 is a magnified view of an exemplary wound pressure display, such as the pressure display shown in FIG. 5.

As pressure-sensing negative pressure therapy sponge embodiment is compressed, a change in polarity, resistance and/or voltage will be captured by a monitor/controller, as shown. Associated monitor/controller software or other programming may apply an algorithm converting the sensed changes to pressures (e.g., mmHg) and may also display to a user wound pressures in or surrounding the sponge, such as but not limited to in the manner of a pressure heat map as shown in FIGS. 5-6.

Electrical power for the monitor/controller may be supplied by a portable battery, such as but not limited to coin batteries or lithium ion batteries to provide portability. The voltage (likely below around 5 V) will not be high enough to be sensed by the patient. The electroactive coating will be able to bend with the sponge without significantly altering the resistance in the system. If only the surface of the sponge is coated, a second coating may be applied to provide an encapsulation layer.

Pressure sensing may be continuous or intermittent as current is pulsed across the system. The electroactive coating may be connected to an adapter/controller. Non-limiting adapter/controller examples include a FFC-FPC (SMT) adapter to a micro PCB with Bluetooth capability. The adapter may also be directly connected to the pressure display monitor or pump display.

Sensing pressure within the sponge or wound provides, among other things, information that may be used to further customize the treatment of a given wound. The primary goal of the dressing design and suction pressure is to achieve a uniform distribution of tissue deformation in the surface of the wounded tissue. Larger sponge pore sizes may result in greater microdeformation and fluid removal. Smaller sponge pore sizes may lead to greater macrodeformation. Monitoring and presenting pressure data to a user will permit the user to adjust the negative pressure applied from the associated vacuum source during NWPT to create the most ideal negative and positive pressure balance to optimize wound healing.

When pressure monitoring/reporting is provided, there may be an alarm associated with the monitor/controller that prevents too much positive pressure (e.g., as indicated by red on the heat map of FIGS. 5-6) which may cause an excessive ischemic environment within the wound tissues. The alarm may also alert a user when too little negative pressure is in the sponge, as such a condition may result in less than adequate fluid removal and an increased infection risk. Each wound may have particular pressure parameters that will accelerate wound healing.

One important aspect of the exemplary pressure sensing negative pressure therapy sponge embodiments described and shown herein is that pressure is being sensed at the wound interface and not at a remote pump outside the wound. The heat map or other pressure indicating display will also allow a user to monitor the three dimensional size of the wound and monitor healing progress. Changes in wound size may be plotted against the pressures the wound faces to create the greatest rate of reduction in wound size.

Figure 8:
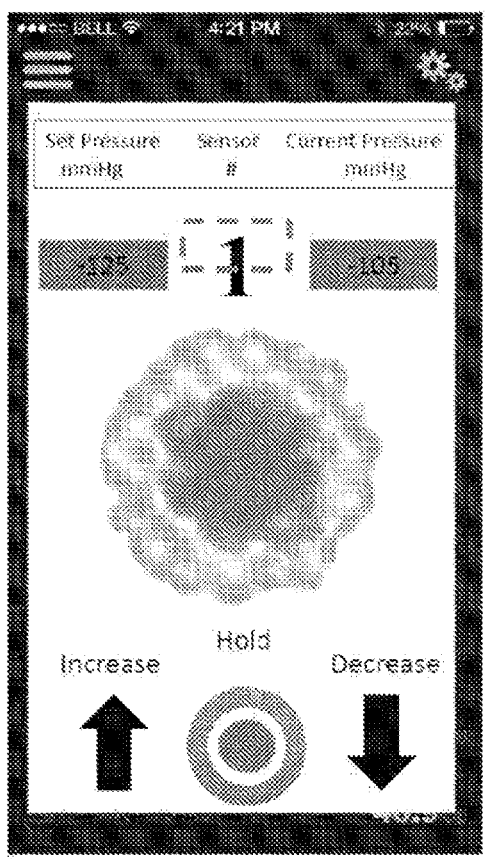
FIG. 8 illustrates another exemplary monitor controller in the form of a smart phone for receiving data from a sponge-placed sensor, and for remotely controlling the negative pressure level produced by an associated NPWT device.

As indicated in FIG. 8, a monitor/controller may be in the form of a smart phone or similar portable device provided with an appropriate application so that pressure information associated with a sponge in a wound may be observed remotely and/or by multiple personnel. In such a case, the monitor/controller may be equipped with Bluetooth® communication capability or may include some other communication protocol having low-power consumption.

By using an appropriately programmed monitor/controller, such as the exemplary monitor/controller shown in FIG. 8, a user could remotely alter sponge pressures by adjusting the negative pressure applied thereto by a connected NPWT pump. Additionally, since real time sponge pressures may be observed, the need for large and expensive pumps may be reduced as more cost effective sources of negative pressure (e.g., wall suction) may be implemented. Normal skin breakdown surrounding the wound being treated can also be monitored for excessive pressures to prevent skin breakdown. In addition to pressure sensing capabilities, an exemplary negative pressure therapy sponge embodiment may also be capable of sensing other characteristics such as but not limited to temperature, pH, glucose and growth factor, which sensed characteristics may be used to, for example, notify a user of an increasing risk of infection, metalloproteinases presence, or other inhibitors to wound healing. An exemplary negative pressure therapy sponge embodiment may also be coated with microspheres to allow the sponge to be drug eluding and deliver growth factors such as VEGF, IGF, FGF or other angiogenic, fibroblastic, or tissue promoting agents.

Figure 9:
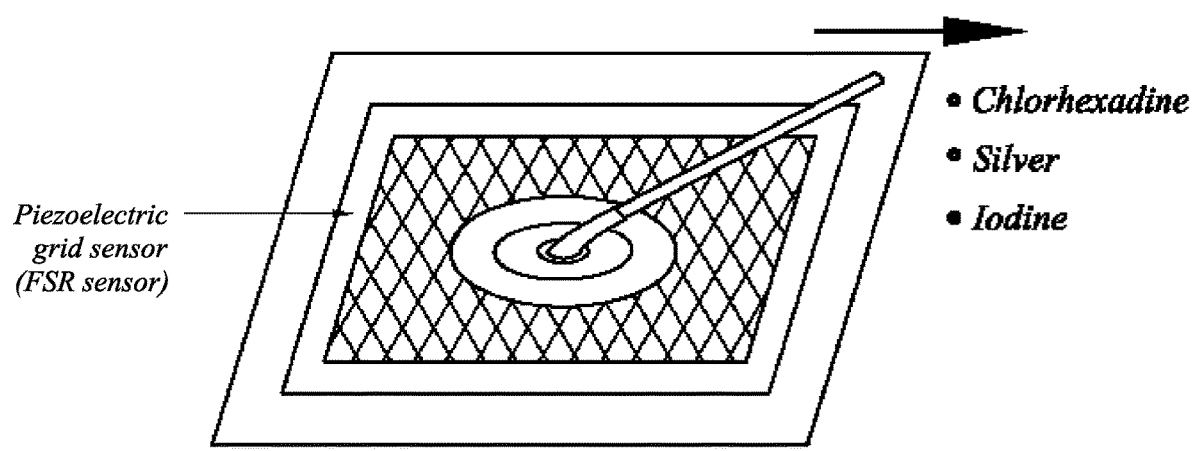
FIG. 9 is a magnified view of one exemplary film and sensor that may form an outer (exposed) surface of an exemplary negative pressure therapy sponge embodiment.

In order to produce adequate negative pressure within a wound to be treated, a closed or substantially closed system must generally be provided. In one exemplary embodiment as represented in FIG. 9, a film such as a clear polyurethane, polyethylene, silicone, acrylate or combination film may be placed over an exemplary negative pressure therapy sponge embodiment while the sponge resides in a wound to be treated so as to create closed system. The film may include an adhesive and may be similar to commercial products like Tegaderm™ tape. The film may also have semipermeable membranes.

Chlorhexidine or a similar antimicrobial substance(s) may be applied to an exemplary film and/or to the adhesive on the film in contact with the skin surrounding the wound. As shown in FIG. 9, an exemplary film may also include piezoelectric or other sensor elements. For example, a piezoelectric coating may be placed on the entire sheet of film or only on a central portion. The provided sensor may also be cut or trimmed so the sensor only covers the sponge surface area. The area of the film that overlies the sponge will then be capable of providing pressure readings from very close to the wound interface. Again, a display of pressures may be presented to a user to facilitate the optimization of NPWT pressure.

Figure 10:
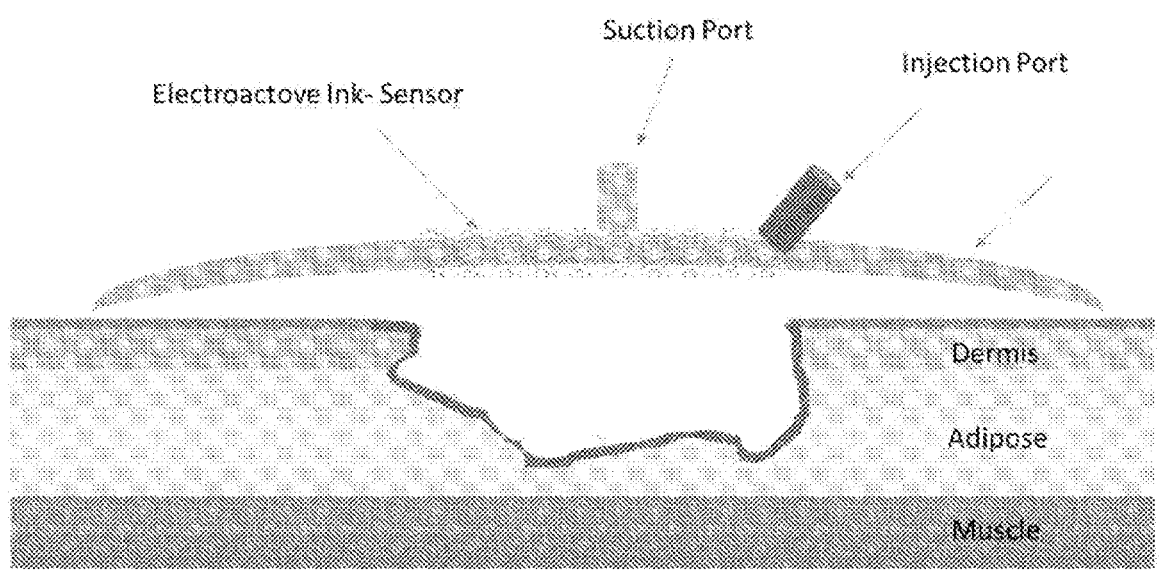
FIG. 10 illustrates another exemplary method of producing a custom negative pressure therapy sponge, wherein a sensor/film may be placed over a wound prior to injecting foam material into the wound.
Figure 11:
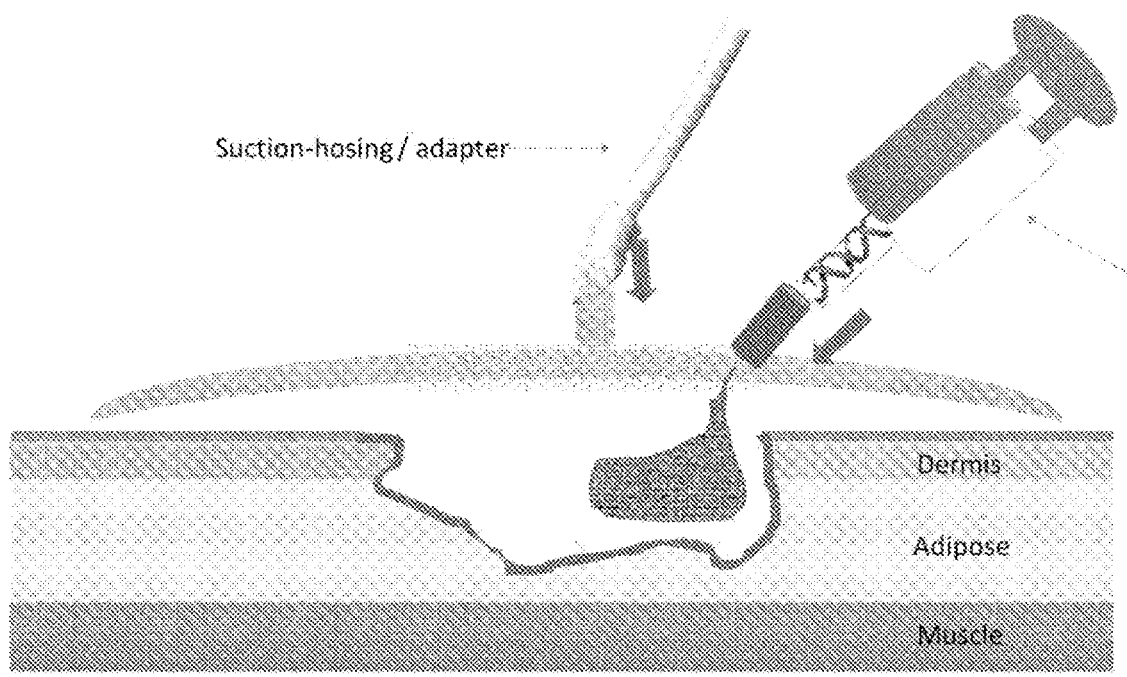
FIG. 11 depicts the connection of suction hosing to a port on the sensor/film of FIG. 10, along with foam injection through another port on the sensor/film.
Figure 12:
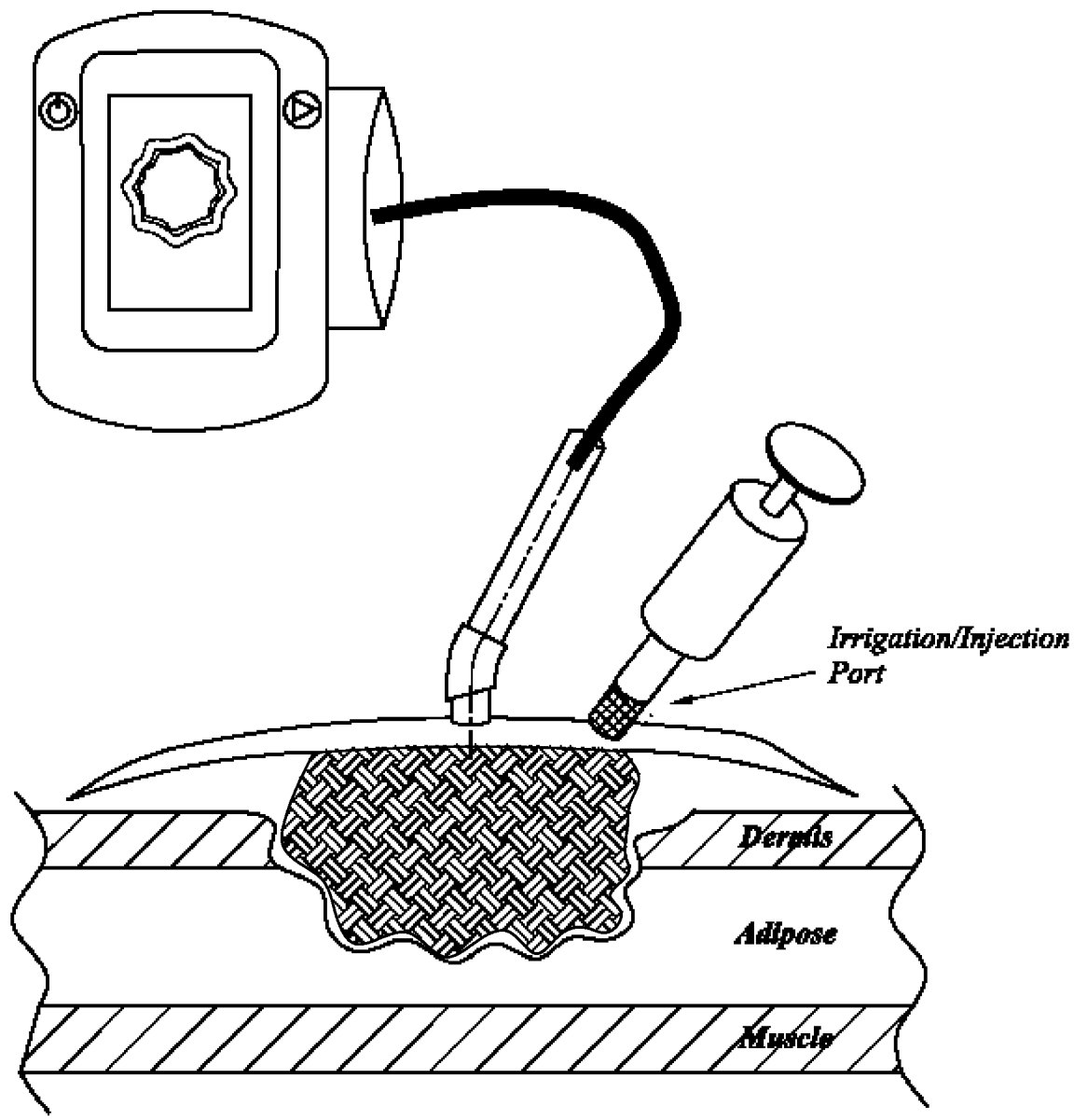
FIG. 12 shows a fully-formed exemplary negative pressure therapy sponge within the wound of FIGS. 10-11, in addition to a monitor/controller connected to the sensor of the sensor/film and a suction device connected to the port previously used to inject the foam.

An alternative technique for creating an exemplary custom negative pressure therapy sponge within a wound to be treated is depicted in FIGS. 10-12. The typical process for placing a known negative pressure therapy sponge in a wound and then applying a wound vacuum thereto to create a negative pressure, involves first applying the polyurethane sponge after it is cut roughly to size. Upon placement in the wound, the sponge commonly sticks out in many places. Thus, a second person is usually required, such that one person can hold the sponge in place while the other person places the overlying tape/dressing. A hole is next cut in the dressing and a pump adapter and hose is applied (see circular disk with hose attached in FIGS. 5 and 9). Sometimes it is necessary to add multiple small pieces of tape to hold the sponges in place and it is a race against fluid seeping out the edges before the vacuum is turned on. This seepage ruins the seal and then one has to spend time finding where the leak is.

Consequently, the exemplary embodiment illustrated in FIGS. 10-12 is designed to overcome these problems by essentially reversing the typical steps involved in placing a negative pressure therapy sponge in a wound. More particularly, and as represented in FIGS. 10-12, an adhesive-backed film is first applied over the wound to produce a good seal on normal (non-wounded) skin, or a non-adhesive-backed film is taped to the normal skin. The film includes at least an injection port through which foam may be applied into the wound in a manner as described above. The film may also include a suction port. With the film in place (see FIG. 10), foam may be applied through the injection port and into the wound (see FIG. 11), whereafter the foam components will react and expand to form a custom negative pressure therapy sponge that conforms to and fills the wound (see FIG. 12). Such an arrangement eliminates the need for multiple sponges and for the assistance an additional person during application, as well as the leaks common to known techniques and systems.

As indicated in FIG. 10, a pressure sensor may be a part of the film, for any of the purposes described above. As indicated in FIG. 12, an adapter and associated suction hosing may be attached to the suction port that passes through the film to permit the subsequent application of negative pressure to the wound and the formed sponge during the NPWT process. The injection port may be used multiple times and may also act as an irrigation port to allow removal of debris from the sponge, or as a conduit for delivering medications/therapies (e.g., for antibiotic irrigation).

In addition to wound therapy as previously described, it is contemplated that exemplary negative pressure therapy sponge and system embodiments may be used in the treatment of burn scar reduction, and hypertrophic or keloid scarring where pressure is a main source of treatment. An exemplary pressure-sensing negative pressure therapy sponge may also be placed on top of an incision to take tension off the repair and optimize aesthetic outcomes. Applying the correct amount of pressure while limiting patient discomfort can be customized to each individual. Pressure-sensing negative pressure therapy sponge embodiments may also be used in custom orthotics such as prosthesis, shoes, inserts, and padding. In such applications, an exemplary pressure-sensing negative pressure therapy sponge may alert a user when excessive pressures leading to skin breakdown might occur. Such a use of an exemplary pressure-sensing negative pressure therapy sponge may also optimize comfort or wear-ability of a prosthetic or orthotic device.

The pressure-sensing foam used to create an exemplary pressure-sensing negative pressure therapy sponge may also be used in the treatment of deformational or positional plagiocephaly. Such a foam may replace existing foams on market and allow for custom application of a molding helmet at the time of patient evaluation. The pressure sensing capability of such a foam inside the helmet could alert the treating individual of excessive pressures during the head molding/shaping process as the calvarium enlarges. The pressure sensing capability of such a foam may also notify a user when the head shape is optimal or when the foam needs to be adjusted. The use of such a foam may also reduce discomfort, ulceration and erythema, and may optimize fit to the underlying tissue/bone. Larger custom open cell memory foam applications may be used in the operating theater for patients along areas prone to break down such as elbows, hips, knees and head during surgery. The custom foam may be placed in splints and casts with pressure reading to prevent skin breakdown, ulceration, or compartment syndrome. There may be applications in the veterinary environment such as the treatment of equine wounds. In addition to the foregoing, in alternative embodiments the sensor or sensing element is included in a layer within the sponge (not necessarily on surface, circumference or coated within). The sensor or sensing element may also be in the form of one or more columns under the port that can be cut to varying length corresponding to the depth of the wound. Such a column preferably has a different rigidity than the surrounding sponge to help assess the pressure being observed at various depths of the wound (sort of like a tsunami buoy system). In yet further alternative embodiments, the pump automatically or dynamically changes the 'flow' within the system to ensure that the pressure seen at or near the bottom of the sensor is sufficient or ideal for wound healing specific to the wound being treated. In such embodiments, the number of 'alerts' and 'stoppages' of the pump is reduced as compared with conventional wound vac pumps, as such alerts and stoppages tend to lead to patient dissatisfaction (e.g., disrupted sleep) and device failure (e.g., from overlying tape getting too saturated and leaking from pump inactivity).

Although the invention has been described in conjunction with specific preferred and other embodiments, it is evident that many substitutions, alternatives and variations will be apparent to those skilled in the art in light of the foregoing description. Accordingly, the invention is intended to embrace all of the alternatives and variations that fall within the spirit and scope of the appended claims. For example, it should be understood that, in accordance with the various alternative embodiments described herein, various systems, and uses and methods based on such systems, may be obtained. The various refinements and alternative and additional features also described may be combined to provide additional advantageous combinations and the like in accordance with the present invention. Also as will be understood by those skilled in the art based on the foregoing description, various aspects of the preferred embodiments may be used in various subcombinations to achieve at least certain of the benefits and attributes described herein, and such subcombinations also are within the scope of the present invention. All such refinements, enhancements and further uses of the present invention are within the scope of the present invention.

What is claimed is:

1. A negative pressure therapy system for a wound environment comprising:
   a) a pump adapted to generate a negative pressure for the wound environment;
   b) a film connected to the pump and positioned outward from a negative pressure sponge conforming to contours of the wound environment; the film forming a seal creating the negative pressure wound environment and further comprising one or more pressure sensors adapted to sense positive, negative and zero pressures associated with the wound environment and communicate wirelessly with a monitor/controller remote from the one or more pressure sensors, wherein the one or more pressure sensors comprises a coating of force-sensing resistors applied to the film; and
   c) the monitor/controller intercommunicating with the one or more pressure sensors and the pump; the monitor/controller comprising software adapted to:
      i) quantify the positive, negative and zero pressures sensed by the one or more pressure sensors;
      ii) cause the controller to automatically control the negative pressures supplied by the pump to the wound environment, wherein the controller's automatic control is dependent on the positive, negative and zero pressures sensed by the one or more pressure sensors; and
      iii) create a visual graphic depiction on the monitor of simultaneous negative, positive and zero pressures associated with the wound environment, wherein the visual graphic depiction assists a user in remotely and manually controlling the negative, positive and zero pressures of the wound environment and negative pressure supplied by the pump to the wound environment.

2. The negative pressure therapy system of claim 1 further comprising at least one sensor adapted to sense one or more of the following:
   a) temperature;
   b) pH;
   c) glucose; and/or
   d) growth factor.

3. The negative pressure therapy system of claim 2, wherein the negative pressure sponge includes one or more of the following:
   a) antimicrobials;
   b) rigidity agents;
   c) stem cells;
   d) growth factors;
   e) wound healing enhancers;
   f) debriding agents;
   g) angiogenic agents;
   h) fibroblastic agents;
   i) tissue promoting agents; and/or
   j) pharmaceutical agents.

4. The negative pressure therapy system of claim 3, wherein a multi-component liquid is delivered to the wound environment to create the negative pressure sponge conforming to contours of the wound environment.

5. The negative pressure therapy systems of claim 4, wherein the film comprises an injection port.

6. A negative pressure therapy system for a wound environment comprising:
   a) a pump adapted to generate a negative pressure for the wound environment;
   b) a film connected to the pump and positioned outward from a negative pressure sponge conforming to contours of the wound environment; the film forming a seal creating the negative pressure wound environment and further comprising one or more pressure sensors adapted to sense positive, negative and zero pressures associated with the wound environment and communicate wirelessly with a monitor/controller remote from the one or more pressure sensors, wherein the one or more pressure sensors comprises a coating of force-sensing resistors applied to the film; and
   c) the monitor/controller intercommunicating with the one or more pressure sensors and the pump.

7. The negative pressure therapy system for a wound environment of claim 6, wherein the monitor/controller comprising software adapted to:
   a) quantify the positive, negative and zero pressures sensed by the one or more pressure sensors;
   b) cause the controller to automatically control the negative pressures supplied by the pump to the wound environment, wherein the controller's automatic control is dependent on the positive, negative and zero pressures sensed by the one or more pressure sensors; and
   c) create a visual graphic depiction on the monitor of simultaneous negative, positive and zero pressures associated with the wound environment, wherein the visual graphic depiction assists a user in remotely and manually controlling the negative, positive and zero pressures of the wound environment and negative pressure supplied by the pump to the wound environment.

8. The negative pressure therapy system of claim 7 further comprising at least one sensor adapted to sense one or more of the following:

a) temperature;
b) pH;
c) glucose; and/or
d) growth factor.

9. The negative pressure therapy system of claim 8, wherein the negative pressure sponge includes one or more of the following:
   a) antimicrobials;
   b) rigidity agents;
   c) stem cells;
   d) growth factors;
   e) wound healing enhancers;
   f) debriding agents;
   g) angiogenic agents;
   h) fibroblastic agents;
   i) tissue promoting agents; and/or
   j) pharmaceutical agents.

10. The negative pressure therapy system of claim 9, wherein a multi-component liquid is delivered to the wound environment to create the negative pressure sponge conforming to contours of the wound environment.

11. The negative pressure therapy systems of claim 10, wherein the film comprises an injection port.

12. A system adapted to generate a negative pressure for a wound environment; the system comprising:
   a) a pump adapted to generate a negative pressure for the wound environment;
   b) a film connected to the pump and positioned outward from a negative pressure sponge conforming to contours of the wound environment, wherein the film creates a seal for the wound environment;
   c) one or more pressure sensors attached to the film and adapted to sense positive, negative and zero pressures associated with the wound environment, wherein the one or more pressure sensors comprises a coating of force-sensing resistors applied to the film; and
   d) a monitor/controller intercommunicating wirelessly with the one or more pressure sensors and the pump controlling adjustment of the positive, negative and zero pressures associated with the wound environment.

13. The system adapted to generate a negative pressure for a wound environment of claim 12, wherein the monitor/controller comprising software adapted to:
   a quantify the positive, negative and zero pressures sensed by the one or more pressure sensors;
   b) cause the controller to automatically control the negative pressures supplied by the pump to the wound environment, wherein the controller's automatic control is dependent on the positive, negative and zero pressures sensed by the one or more pressure sensors; and
   c) create a visual graphic depiction on the monitor of simultaneous negative, positive and zero pressures associated with the wound environment, wherein the visual graphic depiction assists a user in remotely and manually controlling the negative, positive and zero pressures of the wound environment and negative pressure supplied by the pump to the wound environment.

14. The system adapted to generate a negative pressure for a wound environment of claim 13, wherein the film is trimmed to fit the exposed surface area of the wound environment.

* * * * *